United States Patent
Maetani et al.

(10) Patent No.: US 10,092,952 B2
(45) Date of Patent: Oct. 9, 2018

(54) METHOD AND APPARATUS FOR MEASURING APPARENT DENSITY OF METAL POWDER, METHOD AND APPARATUS FOR PRODUCING MIXED POWDER, AND METHOD AND APPARATUS FOR PRODUCING POWDER COMPACT

(75) Inventors: Toshio Maetani, Chiba (JP); Hiroharu Kato, Kobe (JP)

(73) Assignee: JFE STEEL CORPORATION, Tokyo (JP)

( * ) Notice: Subject to any disclaimer, the term of this patent is extended or adjusted under 35 U.S.C. 154(b) by 854 days.

(21) Appl. No.: 14/353,621

(22) PCT Filed: May 16, 2012

(86) PCT No.: PCT/JP2012/063104
§ 371 (c)(1),
(2), (4) Date: Jun. 30, 2014

(87) PCT Pub. No.: WO2013/061642
PCT Pub. Date: May 2, 2013

(65) Prior Publication Data
US 2014/0314615 A1    Oct. 23, 2014

(30) Foreign Application Priority Data
Oct. 24, 2011   (JP) ................................ 2011-232636

(51) Int. Cl.
*B22F 3/00* (2006.01)
*B22F 3/02* (2006.01)
(Continued)

(52) U.S. Cl.
CPC .............. *B22F 3/003* (2013.01); *B22F 3/02* (2013.01); *B22F 3/03* (2013.01); *B30B 15/302* (2013.01);
(Continued)

(58) Field of Classification Search
CPC .... G01N 15/0656; G01N 27/023; B22F 3/003
(Continued)

(56) References Cited

U.S. PATENT DOCUMENTS 5,793,199 A * 8/1998 Kasahara ........... G01N 15/0656
324/204
2009/0237095 A1  9/2009 Takeno et al.

FOREIGN PATENT DOCUMENTS

EP    0 773 440 A1   5/1997
EP    1 020 285 A2   7/2000
(Continued)

OTHER PUBLICATIONS

Dec. 4, 2014 Extended Search Report issued in European Application No. 12 84 2781.2.
International Search Report issued in International Application No. PCT/JP2012/063104 dated Aug. 14, 2012.

*Primary Examiner* — Weiping Zhu
(74) *Attorney, Agent, or Firm* — Oliff PLC

(57) ABSTRACT

A method for measuring an apparent density of a metal powder includes holding a metal powder in a vessel, applying an alternating magnetic flux to the metal powder using an exciting coil disposed outside the vessel, detecting the alternating magnetic flux passed through the metal powder using a search coil disposed outside the vessel, and determining an apparent density of the metal powder from an amplitude of the detected alternating magnetic flux using a calibration curve representing a correlation between the apparent density of the metal powder and the amplitude of an alternating magnetic flux prepared in advance. The method enables to measure the apparent density of a metal powder with a high precision in an on-line and non-contact manner without stopping a process of producing a mixed powder or a process of producing a powder compact.

7 Claims, 4 Drawing Sheets

(51) Int. Cl.
*B30B 15/30* (2006.01)
*G01N 9/00* (2006.01)
*G01N 15/06* (2006.01)
*B22F 3/03* (2006.01)
*G01N 27/72* (2006.01)
*G01N 9/24* (2006.01)

(52) U.S. Cl.
CPC ............ *B30B 15/304* (2013.01); *G01N 9/00* (2013.01); *G01N 15/0656* (2013.01); *G01N 9/24* (2013.01); *G01N 27/72* (2013.01)

(58) Field of Classification Search
USPC ...................................................... 73/861.73
See application file for complete search history.

(56) References Cited

FOREIGN PATENT DOCUMENTS

| | | |
|---|---|---|
| JP | A-51-46999 | 4/1976 |
| JP | A-53-66257 | 6/1978 |
| JP | A-59-65759 | 4/1984 |
| JP | H06-229984 A | 8/1994 |
| JP | U-7-10926 | 2/1995 |
| JP | A-8-167519 | 6/1996 |
| JP | A-9-133652 | 5/1997 |
| JP | A-9-264833 | 10/1997 |
| JP | A-2004-292861 | 10/2004 |
| JP | A-2005-199306 | 7/2005 |
| JP | 2008-008885 A | 1/2008 |
| JP | A-2008-232706 | 10/2008 |

* cited by examiner (a)

(b)

METHOD AND APPARATUS FOR MEASURING APPARENT DENSITY OF METAL POWDER, METHOD AND APPARATUS FOR PRODUCING MIXED POWDER, AND METHOD AND APPARATUS FOR PRODUCING POWDER COMPACT

BACKGROUND OF THE INVENTION

1. Field of the Invention

The present invention relates to a method and apparatus for measuring an apparent density of a metal powder or a mixed powder containing a metal powder. In particular, the present invention relates to a method for measuring an apparent density of a metal powder in an on-line manner without stopping i) a process of producing the metal powder or a mixed powder containing the metal powder by mixing a raw material powder and auxiliary raw materials, which may be powders or liquids, with each other with a specified ratio using a mixer such that the metal powder or the mixed powder has a desired apparent density, or ii) a process of producing a powder compact. The present invention also relates to a method for producing a mixed powder having a desired apparent density using the above-described measurement method and a method for producing a powder compact.

2. Description of the Related Art

Powder metallurgy technology is a technology in which a metal powder serving as a raw material is filled in a die having a predetermined shape, compacted into a powder compact, and then sintered into a sintered compact. By further machining the sintered compact with a machining tool, when it is required, a machine part having a predetermined size and shape is produced. In the case where a high strength is required, a heat treatment such as carburizing or bright quenching may be performed after the sintering or the machining.

In recent years, with the advance of powder metallurgy technology, machine parts having complicated shapes have been produced in so-called near net shapes or in the shapes very close to their finished shapes with a high dimensional accuracy. Therefore, the machining can be simplified compared with that previously required or can be omitted and thus the production cost can be significantly reduced. Furthermore, a mixed powder produced by adding a graphite powder, an alloy powder, a lubricant, and the like to a metal powder in accordance with the intended purpose is used. Appropriate selection of types of powders serving as raw materials and various additives allow the production of machine parts having various characteristics suitable for the intended applications. With the above-described advance of technology, various machine parts produced using the powder metallurgy technology are used in various fields today.

The variations in the size, weight, and density of powder compacts before sintering cause variations in the size and characteristics of the sintered compacts, or the machine parts, that become finished products. Therefore, the variations in the size, weight, and density of powder compacts before sintering are preferably suppressed as much as possible to improve the quality of the machine parts. The variations in the size, weight, and density of the powder compacts mainly result from the variation in the filling density of the powder serving as a raw material filled in the die. To suppress the variation in the filling density, it is quite effective to stabilize the apparent density of the powder serving as a raw material. That is, the stability of the size and characteristics of the sintered compacts or the machine parts significantly depend on the stability of the apparent density of the powder serving as a raw material.

As described above, to produce high-quality machine parts having desired characteristics suitable for the intended applications and small variations in size and the like using powder metallurgy technology, it is quite important to stabilize the apparent density of the powder serving as a raw material.

Herein, the apparent density of a metal powder is generally measured by using the method specified in JIS Z 2504:2000. In this method, the apparent density of a powder is determined by filling the powder to be measured in a vessel having a specified volume under a specified condition, measuring the weight of the powder in the vessel, and dividing the measured weight of the powder by the volume of the vessel.

However, in this method for measuring the apparent density of a powder specified in JIS Z 2504:2000, the powder to be measured needs to be sampled. A powder in a mixer, hopper, or feeder can be subjected to the sampling measurement. In the sampling measurement, however, a mixing or a compacting operation needs to be temporarily stopped to perform the sampling. Accordingly, the apparent density cannot be continuously measured in an on-line manner.

Under such circumstances, for example, Japanese Unexamined Patent Application Publication No. 2005-199306 (Patent Document 1) discloses an apparatus for automatically measuring an apparent density of a metal powder for powder compacts. In the technology disclosed in Patent Document 1, a metal powder compacting apparatus including a feeder that holds a metal powder supplied from a powder supplying means and repeatedly performs an operation of moving the metal powder in the side direction and dropping in a cavity of a die to fill the die with the metal powder. The apparent density of the metal powder held in the feeder is calculated based on a capacitance of the metal powder held in the feeder measured by a powder capacitance measurement means. Patent Document 1 describes that this technology enables to quickly measure the apparent density of a metal powder for powder compacts without stopping fundamental steps of the powder compacting process.

SUMMARY OF THE INVENTION

According to the technology disclosed in Patent Document 1, the apparent density can be measured in an on-line manner in a powder compact manufacturing line. However, in this technology, a rod-shaped probe including a pair of electrodes with an insulator therebetween is used as means for measuring the capacitance of the metal powder held in the feeder. By inserting the probe into the feeder, the capacitance of the metal powder held in the feeder is measured. That is, in the technology disclosed in Patent Document 1, the probe, which is the powder capacitance measurement means, needs to be brought into contact with the metal powder whose apparent density is to be measured. This poses a problem in that the vessel, or the feeder, itself that holds the metal powder has to be converted to install the probe therein.

In the case where the apparent density of a metal powder is determined based on the measured value of the capacitance of the metal powder, there is another problem. That is, the apparent density of a metal powder cannot be accurately measured because the metal powder is an electric conductor and thus the capacitance is extremely low.

When a powder compact is produced in a powder compact manufacturing line, a powder serving as a raw material is normally held in a hopper and transferred to a die through a feeder. After the die is filled with the powder, the powder is subjected to a compaction. However, the apparent density of the powder changes due to environmental factors such as temperature and humidity. Therefore, for example, even if it has been confirmed that a powder has a desired apparent density in a laboratory, the powder may have an apparent density different from the desired apparent density in a manufacturing line whose environment is different from that of the laboratory. This may adversely affect the quality of finished products.

Thus, when a powder compact is produced by compacting a powder, the apparent density of the powder in the powder compact manufacturing line should be kept stable. Furthermore, the apparent density of the powder in a hopper or a feeder is preferably measured in an on-line manner. In this case, even if the apparent density of the powder varies, the variation of the powder compact can be suppressed by suitably adjusting the compacting conditions on the basis of the variation in the apparent density. Consequently, the quality of end products can be maintained.

The apparent density of a powder serving as a raw material is an important factor that determines, for example, the quality of finished products. Accordingly, in a production of a metal powder as a raw material, it is important that a produced powder has a desired apparent density. Normally, a powder serving as a raw material is produced by adding auxiliary raw materials, which may be powders or liquids, to a raw material powder and mixing them together using a mixer. However, the apparent density of the powder in the mixer changes every moment in accordance with the state of mixing. In addition, the apparent density of the powder changes due to environmental factors such as temperature and humidity as described above.

To achieve a desired apparent density, the apparent density of the powder in a mixer is preferably measured in an on-line manner during the mixing operation. If the apparent density can be measured in an on-line manner, the apparent density of the mixed powder can be controlled with high precision by adjusting mixing conditions. For example, mixing is performed while an apparent density of the mixed powder in the mixer is measured, and the mixing operation is stopped when the apparent density reaches a desired apparent density.

For these reasons, in the technical field of powder metallurgy, it is highly desired to establish a method for measuring an apparent density of a powder serving, as a raw material with a high precision in an on-line manner in a powder manufacturing line or in a powder compact manufacturing line.

An exemplary object of the present invention is to advantageously solve the problems of the related art described above. Another object of the present invention is to provide a method for measuring an apparent density of a metal powder with a high precision in an on-line and a non-contact manner without stopping a production process, which may be a process of producing a metal powder or a mixed powder containing a metal powder having a desired apparent density by mixing a raw material powder and auxiliary raw materials, which may be powders or liquids, with each other at a specified ratio using a mixer, or a process of producing a powder compact.

To solve the problems above, the inventors of the present invention have eagerly examined a method for measuring an apparent density of a metal powder held in a vessel with a high precision in a non-contact manner.

Since the relative permeability of a metal is normally higher than that of the air, the magnetic properties in the vessel are believed to be changed as the apparent density of the metal powder held in the vessel, or a volume fraction of the metal powder and the air, is changed. Furthermore, since each substance has a different relative permeability, the magnetic properties of the mixed powder containing a metal powder are also believed to be changed not only as the volume fraction of the metal powder and the air is changed, but also as ratios of various powders, i.e., raw material powder and auxiliary raw materials, contained in the mixed powder change. Accordingly, the inventors have focused on a magnetic flux as a medium capable of measuring the apparent density of a metal powder in a non-contact manner. When a non-magnetic material, which does not affect the magnetic flux, is suitably selected as a material of the vessel, a magnetic flux can be applied to the metal powder held in the vessel from the outside of the vessel and a change in the magnetic flux in the vessel can be detected.

As a result of further examination conducted by the inventors, it has been found that, when an alternating magnetic flux is applied to a metal powder held in a vessel, there is a correlation between the apparent density of the metal powder held in the vessel and the amplitude of the alternating magnetic flux passed through the metal powder. It has been also found that, in a non-contact measurement that uses an alternating magnetic flux as a medium, simple and high-precision measurement can be achieved by disposing an exciting coil and a search coil outside the vessel that holds the metal powder. Herein, the exciting coil generates an alternating magnetic flux to be applied to the metal powder, and the search coil detects the alternating magnetic flux passed through the metal powder.

An experiment for examining the correlation between the apparent density of the metal powder held in the vessel and the amplitude of the alternating magnetic flux passed through the metal powder is described below. As a result of this experiment, the findings of the present invention have been obtained.

Pure iron powder (product name: JIP-300A manufactured by JFE Steel Corporation) was used as a powder to be measured. A stainless steel vessel (type of stainless steel: SUS304) having a width of 100 mm, a length of 130 mm, a height of 60 mm, and a wall thickness of 0.5 mm was prepared. A frame, or a hollow prism, having the same size as that of the stainless steel vessel was fixed above the stainless steel vessel. The powder was charged into the vessel and the frame so that the level of the powder reached about a half the height of the frame. The frame was then moved in a horizontal direction to level off the powder at the upper surface of the vessel. When the powder was charged into the vessel, various apparent densities were provided by adjusting the number of tapping operations performed on an entirety of the vessel and frame before leveling off the powder. Subsequently, an alternating magnetic flux was applied to the powder in the vessel using an exciting coil from the outside of the vessel by oscillating a sinusoidal signal with a frequency of 100 Hz, 1 kHz, or 10 kHz at a set voltage of 10 mVp-p (Vp-p: peak-to-peak potential difference of the voltage waveform). The alternating magnetic flux passed through the powder was detected by a search coil to determine the amplitude of the alternating magnetic flux. The application and detection of the alternating magnetic flux were performed by a method shown in FIG. 4 below.

Furthermore, the apparent density of the powder held in the vessel was measured from the weight of the powder and the volume of the vessel.

FIGS. 1 to 3 are graphs each showing the relationship between the apparent density and the amplitude of alternating magnetic flux. In the graphs, the vertical axis shows the amplitude of the alternating magnetic flux passed through the powder and the horizontal axis shows the apparent density ($Mg/m^3$) determined from the weight of the powder and the volume of the vessel. FIG. 1 shows the case where the frequency of the applied alternating magnetic flux is 100 Hz, FIG. 2 shows the case where the frequency of the applied alternating magnetic flux is 1 kHz, and FIG. 3 shows the case where the frequency of the applied alternating magnetic flux is 10 kHz. As is clear from FIGS. 1 to 3, the amplitude of the alternating magnetic flux substantially linearly increases as the apparent density increases. Thus, a specific correlation is recognized.

The present invention is based on these findings and the gist of the present invention is as follows.

[1] A method for measuring an apparent density of a metal powder which includes holding a metal powder in a vessel; applying an alternating magnetic flux to the metal powder using an exciting coil disposed outside the vessel; detecting an alternating magnetic flux passed through the metal powder using a search coil disposed outside the vessel; and determining an apparent density of the metal powder from an amplitude of the detected alternating magnetic flux using a calibration curve representing a correlation between the apparent density of the metal powder and the amplitude of the alternating magnetic flux prepared in advance.

[2] In the method according to [1], a frequency of the alternating magnetic flux applied to the metal powder may be 10 Hz or more and 10 kHz or less.

[3] In the method according to [1] or [2], the metal powder may be a mixed powder containing a metal powder.

[4] A method for producing a mixed powder containing a metal powder using a mixer which includes performing mixing operation while measuring an apparent density of the mixed powder in the mixer by the method according to [3]; and ending the mixing operation when a predetermined apparent density is achieved.

[5] A method for producing a powder compact in a powder compact manufacturing line which includes filling a die with a mixed powder containing a metal powder; and compacting the mixed powder, wherein an apparent density of the mixed powder in a feeder of the powder compact manufacturing line is measured by the method according to [3] in an on-line manner, and a filling depth of the mixed powder in the die is adjusted in accordance with the measured apparent density.

[6] An apparatus for measuring an apparent density of a metal powder which includes a vessel that holds a metal powder; an exciting coil that applies an alternating magnetic flux to the metal powder, the exciting coil being disposed outside the vessel; a search coil that detects the alternating magnetic flux passed through the metal powder, the search coil being disposed outside the vessel; and a calculator that calculates an apparent density of the metal powder from an amplitude of the alternating magnetic flux detected by the search coil using a correlation between the amplitude and the apparent density of the metal powder derived and stored in advance.

[7] In the apparatus according to [6], the metal powder may be a mixed powder containing a metal powder.

[8] An apparatus for producing a mixed powder containing a metal powder which includes a mixer; an exciting coil that applies an alternating magnetic flux to a mixed powder containing a metal powder in the mixer, the exciting coil being disposed outside the mixer; a search coil that detects the alternating magnetic flux passed through the mixed powder, the search coil being disposed outside the mixer; and a calculator that calculates an apparent density of the mixed powder by inputting an amplitude of the alternating magnetic flux detected by the search coil.

[9] An apparatus for producing a powder compact which includes a die to be filled with a mixed powder containing a metal powder and to compact the mixed powder; a feeder that supplies the mixed powder to the die; an exciting coil that applies an alternating magnetic flux to the mixed powder in the feeder, the exciting coil being disposed outside the feeder; a search coil that detects the alternating magnetic flux passed through the mixed powder, the search coil being disposed outside the feeder; and a calculator that calculates an apparent density of the mixed powder by inputting an amplitude of the alternating magnetic flux detected by the search coil.

According to the present invention, an apparent density of a metal powder can be measured with a high precision using a simple equipment including an alternating magnetic flux generating coil (exciting coil) and an alternating magnetic flux detecting coil (search coil) disposed outside the vessel that holds the metal powder. Therefore, the apparent density of a powder held in a hopper or a feeder of a powder compact manufacturing line can be measured in an on-line manner without stopping the manufacturing line. Furthermore, in the process of producing a mixed powder by mixing a raw material powder and auxiliary raw materials with each other at a specified ratio using a mixer, a mixed powder having a desired apparent density can be produced by measuring, in an on-line manner, the apparent density of the powder mixed in the mixer, which produces industrially significant effects. The present invention can also be applied to the case where the powder held in the vessel is a mixed powder produced by adding a nonmetal powder such as a graphite powder, a lubricant, or the like to a metal powder.

DESCRIPTION OF THE PREFERRED EMBODIMENTS

Figure 1:
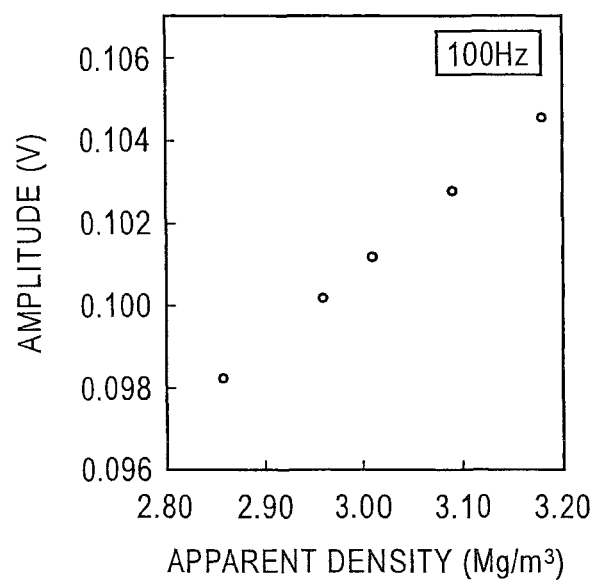
FIG. 1 is a graph showing a correlation between an amplitude (vertical axis: V) of the alternating magnetic flux (frequency: 100 Hz) passed through a powder and an apparent density (horizontal axis: $Mg/m^3$) of the powder.
Figure 2:
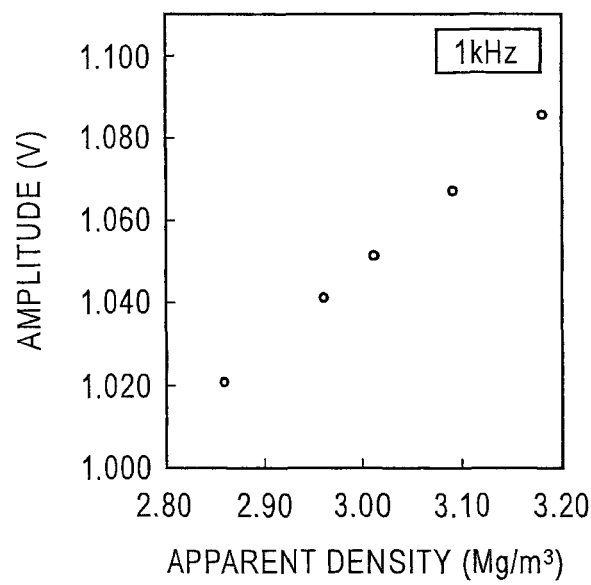
FIG. 2 is a graph showing a correlation between an amplitude of the alternating magnetic flux (frequency: 1 kHz) passed through a powder and an apparent density of the powder.
Figure 3:
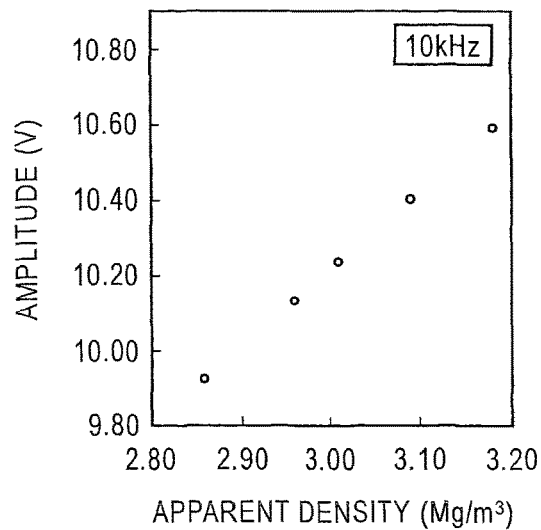
FIG. 3 is a graph showing a correlation between an amplitude of the alternating magnetic flux (frequency: 10 kHz) passed through a powder and an apparent density of the powder.
Figure 4:
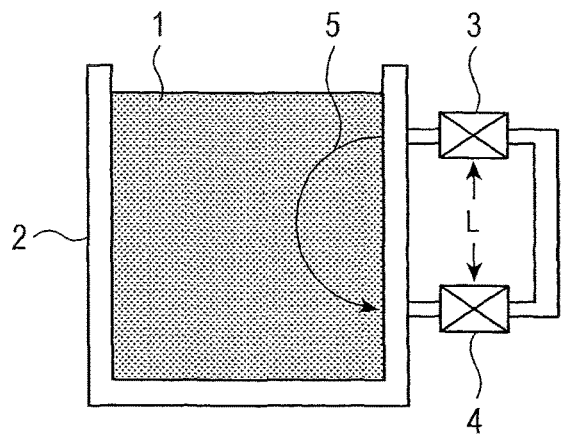
FIG. 4 is a schematic view for describing a method for measuring an apparent density of a metal powder according to the present invention.

A method for measuring an apparent density of a metal powder will now be described. In a method for measuring an apparent density of a metal powder according to the present invention, a metal powder is held in a vessel as shown in FIG. 4; an alternating magnetic flux is applied to the metal powder using an exciting coil disposed outside the vessel; the alternating magnetic flux passed through the metal powder is detected using a search coil disposed outside the vessel; and an apparent density of the metal powder is determined from an amplitude of the detected alternating magnetic flux using a calibration curve representing a correlation between the apparent density of the metal powder and the amplitude of an alternating magnetic flux prepared in advance.

In the present invention, since an alternating magnetic flux is applied to an object to be measured and a change in the alternating magnetic flux caused by the object to be measured is determined, the object to be measured is assumed to be mainly a ferromagnetic material. Accordingly, the object to be measured according to the present invention is mainly a ferromagnetic metal powder. Note that, however, the metal powder according to the present invention is not limited to a powder composed of a single metal but may also be a powder composed of two or more metals mixed with each other, where at least one metal is a ferromagnetic metal, or an alloy powder.

Further, the object to be measured according to the present invention may be a mixed powder containing a metal powder and a powder other than the metal powder. That is, a mixed powder is also regarded as a metal powder in a broad sense. When a powder compact is produced using powder metallurgy technology, a mixed powder produced by adding auxiliary raw materials such as a graphite powder, a lubricant powder, and a binder to a metal powder, which is a principal raw material, is generally used. Even in the case where a mixed powder containing auxiliary raw materials other than a metal powder is used, the measurement method according to the present invention can be applied as long as the mixed powder contains a ferromagnetic metal powder as a principal raw material. Hereinafter, a mixed powder is also referred to as a metal powder unless otherwise specified.

A vessel that holds a metal powder or a mixed powder containing a metal powder (hereinafter, both may be simply referred to as "powder" in a collective manner) is composed of a non-magnetic material. If the vessel is composed of a magnetic material, the vessel affects the alternating magnetic flux generated by an exciting coil and the alternating magnetic flux detected by a search coil, both are disposed outside the vessel. As a result, the alternating magnetic flux cannot be measured accurately. The material of the vessel is not particularly limited as long as the material is a non-magnetic material. For example, austenitic stainless steel, aluminum, a resin, or the like is suitably used. The size, e.g., volume, thickness, or the like, of the vessel is also not particularly limited, but the vessel preferably has a smaller thickness in order to ensure a sufficient amount of magnetic flux that passes through the object to be measured.

Conventionally known coils can be used as the coils disposed outside the vessel as the exciting coil that generates an alternating magnetic flux to be applied to a powder and the search coil that detects the alternating magnetic flux passed through the powder. The number of turns of the exciting coil may be suitably adjusted in accordance with desired alternating magnetic flux to be generated. The number of turns of the search coil may be suitably adjusted in accordance with desired detection sensitivity. These coils preferably include magnetic cores for increasing the magnetic flux. In this case, a magnetic core composed of iron or ferrite may be suitably selected in accordance with the frequency range of the alternating magnetic flux to be applied to the powder.

Figure 5:
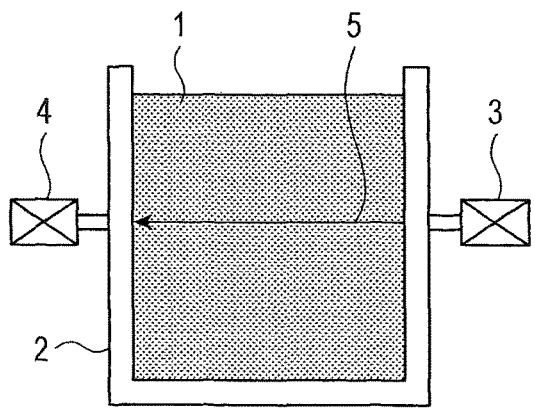
FIG. 5 is a schematic view showing another example of places where an exciting coil and a search coil are disposed outside the vessel in the method for measuring the apparent density of a metal powder according to the present invention.

In FIG. 4, an exciting coil 3 and a search coil 4 are disposed on one side wall of a vessel 2 that holds a powder 1 so as to be arranged in parallel in a vertical direction. When an alternating magnetic flux 5 is generated by the exciting coil 3 while the exciting coil 3 and the search coil 4 are disposed in such a manner, the alternating magnetic flux 5 passes through the powder 1 held in the vessel 2 as indicated by a solid line in FIG. 4 and detected by the search coil 4. In FIG. 5, the exciting coil 3 is disposed on one side wall of the vessel 2 and the search coil 4 is disposed on the other side wall of the vessel 2. In both cases shown in FIGS. 4 and 5, the exciting coil 3 and the search coil 4 may be fixed to the vessel 2 or may be separately disposed without being fixed to the vessel 2. Note that the arrangement of the coils is not limited to the cases shown in FIGS. 4 and 5.

The distance L between the exciting coil 3 and the search coil 4 is not particularly limited as long as the alternating magnetic flux 5 generated by the exciting coil 3 and passed through the powder 1 can be detected by the search coil 4. However, if the distance L is excessively small, the alternating magnetic flux 5 passes through only a limited portion of the powder 1. As a result, it becomes difficult to measure the apparent density of the entire powder 1, or an average apparent density of the powder 1, held in the vessel 2. As a result, an accuracy of the measurement decreases. If the distance L is excessively large, the alternating magnetic flux 5 passed through the powder 1 is not easily detected by the search coil 4, or the sensitivity is decreased, and an accuracy of the measurement decreases. Therefore, preferably, the distance L between the exciting coil 3 and the search coil 4 is appropriately determined in accordance with the type of the powder, which is an object to be measured, the thickness of the vessel, the frequency and an amplitude of the alternating magnetic flux generated by the exciting coil 3, and a detection sensitivity of the search coil 4.

The frequency of the alternating magnetic flux generated by the exciting coil 3 is preferably 10 Hz or more and 10 kHz or less. If the frequency is less than 10 Hz, amplitude of the alternating magnetic flux detected by the search coil 4 decreases and the accuracy of measurement decreases. If the frequency is more than 10 kHz, a deviation in the phase of the alternating magnetic flux detected by the search coil 4 increases and the correlation between the amplitude and the apparent density becomes insufficient. The frequency is more preferably 100 Hz or more and 1 kHz or less.

Figure 6:
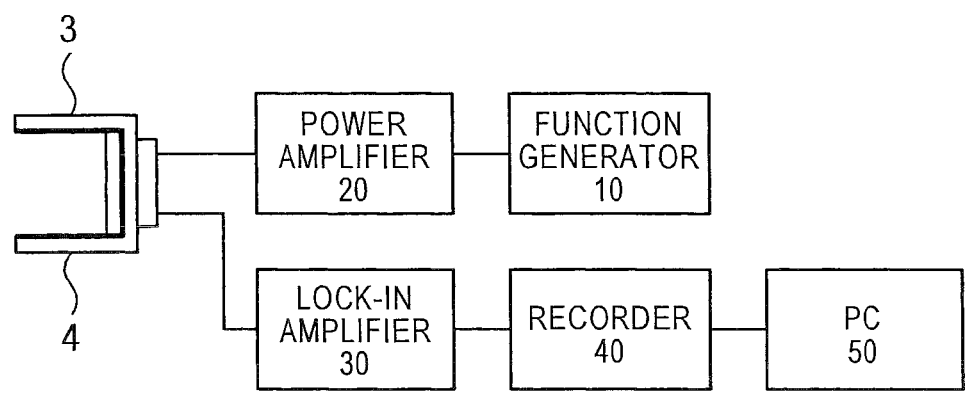
FIG. 6 is a diagram showing an exemplary apparatus suitably used to perform the method for measuring an apparent density of a metal powder according to the present invention.

FIG. 6 shows an exemplary apparatus suitably used to perform the method for measuring the apparent density of a metal powder according to the present invention. This apparatus includes the exciting coil 3 and the search coil 4 described above, a function generator (signal generator) 10, a power amplifier 20, a lock-in amplifier 30, a recorder 40, and a personal computer (PC) 50. This apparatus may be placed on a mobile workbench or the like so as to be readily moved.

The PC 50 functions as a calculator that calculates the apparent density of the metal powder by inputting the amplitude of the alternative magnetic flux detected by the search coil 4. The data of the calibration curve representing the correlation between the apparent density of the powder 1 and the amplitude of the alternating magnetic flux passed through the powder 1 prepared in advance is stored in the PC 50. The calibration curve can be prepared by the following method. That is, for each kind of powders or mixed powders, which are objects to be measured, an alternating magnetic flux is applied to powders having various apparent densities to measure the amplitudes of the alternating magnetic flux passed through the powders. From the measurement data, for example, constants A and B in "Apparent density=Amplitude×A+B" are determined by a least-squares method. Thus, a calibration curve can be prepared for each of the objects to be measured. Obviously, the correlation between the apparent density and the amplitude of the alternating magnetic flux is not limited to a correlation expressed by such a linear function and may be a correlation expressed by a more complicated curved line. The calibration curve may be stored in the PC 50 in the form of a function between the apparent density and the amplitude or coefficients of the function. For example, the above-described constants A and B may be stored in the PC 50 for each kind of the powders. In other words, the PC 50 needs only to be configured so that apparent densities of the metal powders can be calculated from the amplitude of the alternating magnetic flux detected by the search coil using the correlations between the amplitude and the apparent density of the metal powders derived and stored in the PC 50 in advance.

The exciting coil 3 and the search coil 4 are disposed outside the vessel 2 that holds the powder 1 with a specified distance L. A sinusoidal signal generated by the function generator (signal generator) 10 is amplified by the power amplifier 20. An alternating magnetic flux 5 is generated by the exciting coil 3 and applied to the powder 1 held in the vessel 2. The alternating magnetic flux 5 passed through the powder 1 is detected by the search coil 4. The amplitude of the alternating magnetic flux 5 is measured using the lock-in amplifier 30 and recorded by the recorder 40. The amplitude recorded by the recorder 40 is compared with the calibration curve in the PC 50 to determine the apparent density of the powder 1.

As described above, in the present invention, the apparent density of the powder 1 can be measured with a simple apparatus including the exciting coil 3 and the search coil 4 disposed outside the vessel 2, without inserting a probe or the like into the vessel 2 that holds the powder 1. Therefore, according to the present invention, the apparent density of a powder held or filled in a hopper or a feeder can be easily measured in an on-line manner by disposing the exciting coil 3 and the search coil 4 outside the hopper or feeder in a powder compact manufacturing line. If the apparatus is placed on a mobile workbench or the like so as to be readily moved, the apparatus can be moved to the vicinity of the hopper or feeder in the powder compact manufacturing line. The type of the feeder is not restricted. An example of the feeder is a feeder including a feeder box. In other words, the feeder box can be used as the vessel 2.

A method for producing a mixed powder according to the present invention will now be described. A method for producing a mixed powder according to the present invention is performed by using the method for measuring an apparent density according to the present invention described above. In the method for producing a mixed powder according to the present invention, during a production of a mixed powder by mixing a principal raw material powder (metal powder) and auxiliary raw materials with each other using a mixer, an alternating magnetic flux is applied to the mixed powder in the mixer using an exciting coil, which is disposed outside the mixer, i.e., outside of a vessel in which mixing operation of powders is performed. And the alternating magnetic flux passed through the mixed powder is detected by a search coil disposed outside the mixer. The mixing operation is continued until the amplitude of the detected alternating magnetic flux reaches the amplitude that corresponds to a desired apparent density determined using a calibration curve representing the correlation between the apparent density of the powder and the amplitude of the alternating magnetic flux prepared in advance. Thus, a mixed powder having a desired apparent density is produced by the mixer.

In the case where different types of powders are mixed with each other, in general, the apparent density varies as the mixing operation proceeds. For example, when a coarse powder and a fine powder are mixed with each other, the apparent density increases because particles of the fine powder enter the gaps between particles of the coarse powder. When a powder having a large adhesion force is mixed, the apparent density decreases. Furthermore, the apparent density varies with the progress, e.g., the uniformity of the mixed powder, of the mixing operation.

During the production of a mixed powder by mixing a principal raw material powder and auxiliary raw materials, which may be powders or liquids, with each other using a mixer, the apparent density of the mixed powder can be measured in an on-line manner. That is, the apparent density of the powder in the mixer is measured while mixing the powder by using the method for measuring an apparent density according to the present invention. In other words, in the method for producing a powder according to the present invention, the apparent density of the mixed powder can be measured while continuing the mixing operation without stopping the mixer to perform a sampling. Therefore, the operating efficiency for producing a powder can be significantly increased. Furthermore, a mixed powder having a desired apparent density can be produced.

Figure 7:
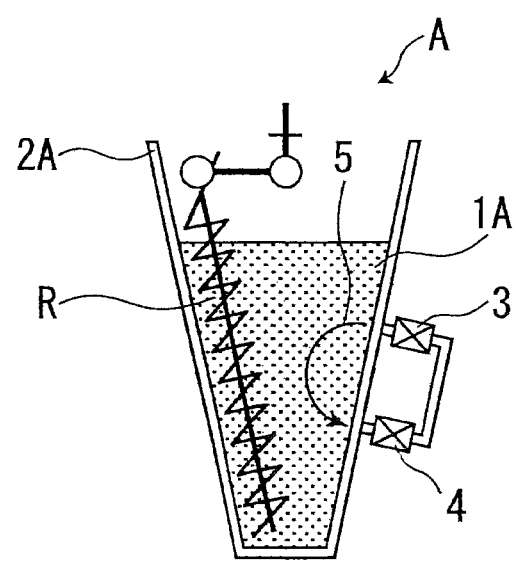
FIG. 7 is a schematic diagram showing a mixed powder producing apparatus according to the present invention.

FIG. 7 shows a conical screw mixer as an exemplary apparatus that can be suitably used to practice the method for producing a mixed powder according to the present invention. This apparatus for producing a mixed powder includes a mixer A installed with the apparent density measuring apparatus shown in FIG. 6. The mixer A has a vessel 2A that holds and mixes a principal raw material powder and auxiliary raw materials, which may be powders or liquids. The vessel 2A is a vessel equipped with a screw R, for example, and performs a function of mixing the powders. Specifically, the mixer A is installed with the exciting coil 3 that applies an alternating magnetic flux to the mixed powder within the vessel 2A and the search coil 4 that detects the alternating magnetic flux 5 passed through the mixed powder 1A, which are both disposed outside the vessel 2A of the mixer A.

The apparatus described above further includes a function generator (signal generator) 10, a power amplifier 20, a lock-in amplifier 30, a recorder 40, and a PC (personal computer) 50, which are not shown in the diagram. The PC 50 is provided as a calculator that calculates an apparent density of the mixed powder 1A by inputting amplitude of the alternating magnetic flux detected by the search coil 4. The functions of the exciting coil 3, search coil 4, function generator (signal generator) 10, power amplifier 20, lock-in amplifier 30, recorder 40, and PC 50 are the same as previously described.

In FIG. 7, the exciting coil 3 and the search coil 4 are disposed on one side wall of the vessel 2A of the mixer A in parallel in a vertical direction. The arrangement of the exciting coil 3 and the search coil 4 is not limited to this example. That is, various arrangements including, for example, an arrangement of disposing the exciting coil 3 on one side wall of the vessel 2A and disposing the search coil 4 on the other side wall of the vessel 2A, may be adopted. Further, the exciting coil 3 and the search coil 3 may be fixed to the vessel 2A or may be separately disposed without fixing to the vessel 2A.

Figure 8:
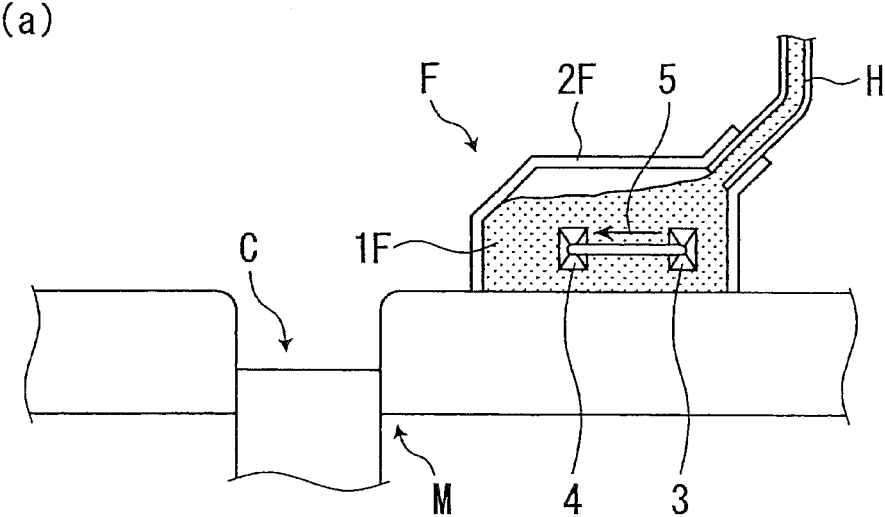
FIG. 8 is a schematic diagram showing a powder compact producing apparatus according to the present invention, wherein (a) is a cross-sectional diagram and (b) is a plane schematic diagram.
Figure 8:
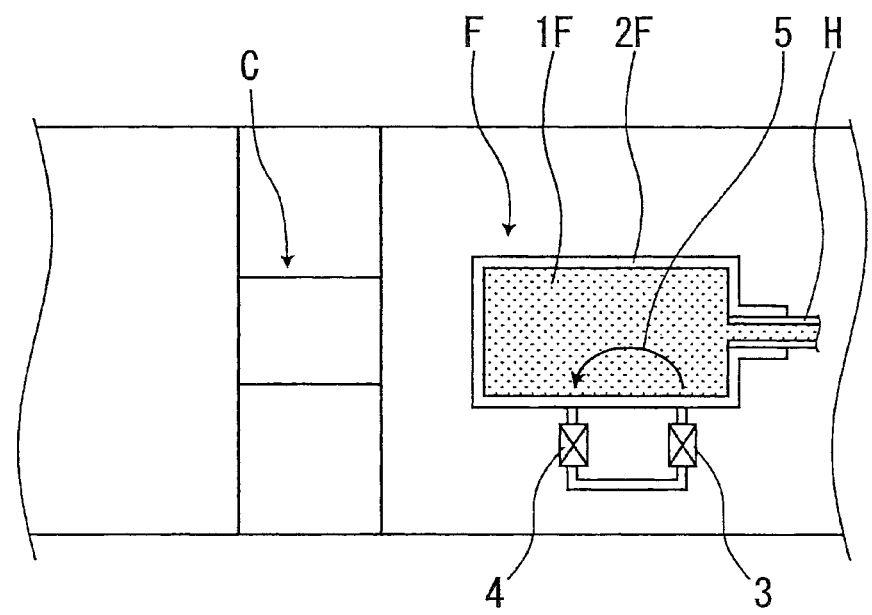

FIG. 8 shows an exemplary apparatus that can be suitably utilized for practicing the method for producing a powder compact according to the present invention, where (a) is a cross-sectional schematic diagram and (b) is a plane schematic diagram. This apparatus for producing a powder compact includes a die M to be filled with a mixed powder containing a metal powder and to compact the mixed powder and a feeder F that supplies the mixed powder to the die M. The feeder F includes a feeder box 2F with an open bottom. A mixed powder stocked in a hopper (not shown) is supplied to the feeder box 2F through a supplying hose H and other components. Then, the mixed powder 1F in the feeder box 2F is filled in a cavity C of the die M by horizontally moving the feeder box 2F to a position above the cavity C of the die M.

The apparatus for producing a powder compact is installed with the apparent density measuring apparatus shown in FIG. 6 at the feeder box 2F. That is, the apparatus includes the exciting coil 3 that applies an alternating magnetic flux to the mixed powder within the feeder box 2F and the search coil 4 that detects the alternating magnetic flux 5 passed through the mixed powder 1F, which are both disposed outside the feeder box 2F.

The apparatus for producing a powder compact according to the present invention further includes a function generator (signal generator) 10, a power amplifier 20, a lock-in amplifier 30, a recorder 40, and a PC (personal computer) 50, which are not shown in the diagram, in addition to the components described above. The PC is provided as a calculator that calculates an apparent density of the mixed powder by inputting amplitude of the alternating magnetic flux detected by the search coil 4. The functions of the exciting coil 3, search coil 4, function generator (signal generator) 10, power amplifier 20, lock-in amplifier 30, recorder 40, and PC 50 are the same as previously described.

In FIG. 8, the exciting coil 3 and the search coil 4 are disposed on one side wall of the feeder box 2F in parallel in a horizontal direction. The arrangement of the exciting coil 3 and the search coil 4 is not limited to this example. That is, various arrangements including, for example, an arrangement of disposing the exciting coil 3 on one side wall of the feeder box 2F and disposing the search coil 4 on the other side wall of the feeder box 2F, may be adopted. Further, the exciting coil 3 and the search coil 3 may be fixed to the feeder box 2F or may be separately disposed without fixing to the feeder box.

Examples (1) Measurement of Apparent Density of Mixed Powder in Mixer

The apparent density of a mixed powder in a mixer was measured with the apparatus shown in FIG. 6. A conical screw mixer (mixing volume: 10 liters) manufactured by Hosokawa Micron Corporation was used as the mixer. An exciting coil 3 and a search coil 4 were disposed outside a SUS304 conical mixing vessel so as to be arranged in a vertical direction. The coils each included a ferrite core. The number of turns of the exciting coil 3 was 100 and that of the search coil 4 was 200. The exciting coil 3 was disposed on the upper side and the search coil 4 was disposed on the lower side so that the distance L between the exciting coil 3 and the search coil 4 was 40 mm. The distance between the bottom of the vessel and the search coil 4 was 100 mm.

A sinusoidal signal (set voltage: 50 mVp-p, frequency: 500 Hz) was generated by a function generator 10 and amplified by a power amplifier 20. An alternating magnetic flux was applied using the exciting coil 3. The alternating magnetic flux passed through a powder held in the vessel was detected by the search coil 4 and the amplitude of the alternating magnetic flux is measured using a lock-in amplifier 30.

As a principal raw material, 9720 g of pure iron powder (product name: JIP-301A manufactured by JFE Steel Corporation) was charged into the mixer. The apparent density of the pure iron powder measured in accordance with JIS Z 2504:2000 was 2.92 Mg/m$^3$.

Subsequently, as auxiliary raw materials, 200 g of copper powder (product name: CE-25, electrolytic copper powder manufactured by Fukuda Metal Foil & Powder Co., Ltd.), 80 g of graphite powder (product name: CPB-K manufactured by Nippon Graphite Industries, Co., Ltd.), and 80 g of zinc stearate (manufactured by NOF Corporation) as a lubricant were charged into the mixer and mixed with each other using a screw having a rotational speed of 180 rpm and an orbital speed of 6 rpm.

To prepare a calibration curve, an alternating magnetic flux detected by the search coil 4 was measured during the mixing operation by the following method. After the mixing was performed for 5 minutes, the mixed powder was discharged. The apparent density of the discharged mixed powder measured in accordance with JIS Z 2504:2000 was 3.05 Mg/m$^3$. The discharged mixed powder was charged into the mixer again. After the mixing was performed for 30 minutes under the above-described conditions, the mixed powder was discharged. The apparent density of the discharged mixed powder measured in accordance with JIS Z 2504:2000 was 3.26 Mg/m$^3$. A calibration curve was prepared from the thus obtained apparent densities and the alternating magnetic flux just before the mixed powder was discharged from the mixer using "Apparent density=Amplitude of alternating magnetic flux×A+B (A, B: constant)". The constants A and B were determined from the measurement results by using a least-squares method. The constant A was 34.946 and the constant B was −14.782.

The target apparent density was set to be 3.20 Mg/m$^3$. The amplitude of the alternating magnetic flux was measured and apparent density determined based on the calibration curve was monitored while the mixing operation was performed by the above-described method. The mixing operation was ended at the time when the monitored apparent density reached the target apparent density and the mixed powder was discharged. The apparent density of the discharged mixed powder was measured in accordance with JIS Z 2504:2000. The mixing operations were performed in three batches. Table 1 shows periods required for the mixing and the measurement result of apparent densities of produced mixed powders.

Furthermore, mixing operations were performed in three batches in the same manner using another pure iron powder as a principal raw material. Another pure iron powder had an apparent density of 2.98 Mg/m³ measured in accordance with JIS Z 2504:2000. Table 1 shows the period required for the mixing and the measurement result of the apparent density of the produced mixed powder. The apparent densities of the produced mixed powders were 3.19 to 3.21 Mg/m³, which were close to the target apparent density of 3.20 Mg/m³. Accordingly, the apparent density of the mixed powder could be monitored in an on-line manner by using the method for measuring an apparent density according to the present invention. Furthermore, a mixed powder having a target apparent density could be produced by adjusting the mixing time.

TABLE 1

| Batch No. | Apparent density of pure iron powder *1 (Mg/m³) | Mixing time (min) | Apparent density of mixed powder *1 (Mg/m³) |
|---|---|---|---|
| 1 | 2.92 | 18.0 | 3.20 |
| 2 | 2.92 | 18.6 | 3.21 |
| 3 | 2.92 | 17.4 | 3.20 |
| 4 | 2.98 | 16.6 | 3.20 |
| 5 | 2.98 | 16.9 | 3.20 |
| 6 | 2.98 | 16.1 | 3.19 |

*1 Apparent density measured in accordance with JIS Z 2504:2000

(2) Measurement of Apparent Density of Powder in Feeder

A mixed powder having the same composition as that of the mixed powder used in "(1) Measurement of Apparent Density of Mixed Powder in Mixer" was charged into a raw material hopper of a powder compact manufacturing line. The apparatus shown in FIG. 6 was installed to a feeder that communicates with the raw material hopper to measure the apparent density of the mixed powder in the feeder. The numbers of turns of the exciting coil 3 and the search coil 4, the distance L between the exciting coil 3 and the search coil 4, and the measurement conditions were the same as those used in "(1) Measurement of Apparent Density of Mixed Powder in Mixer". The apparent density of the mixed powder in the feeder during the compaction operation was monitored using the calibration curve "Apparent density=Amplitude of alternating magnetic flux×A+B (A=34.946, B=−14.782" prepared in (1). After a die was filled with the mixed powder held in the feeder, the mixed powder was compacted into a ring-shaped compact having an outer diameter of 60 mm, an inner diameter of 20 mm, and a height of 20 mm. The resultant compact was weighed using an electronic balance.

Mixed powders having apparent densities measured in accordance with JIS Z 2504:2000 of 3.20 Mg/m³ and 3.26 Mg/m³ were prepared and 20 compacts were produced from each of the mixed powders. After the die was filled with the mixed powder held in the feeder, the mixed powder was compacted under the condition A or B below. Under the condition A, the mixed powder was compacted under a predetermined compacting condition, i.e., a compacting condition including no adjustment of the filling depth. Under the condition B, the apparent density of the mixed powder in the feeder during the compaction operation was monitored and the mixed powder was compacted while the filling amount was controlled by adjusting the filling depth in accordance with the monitored apparent density. That is, under the condition B, the filling depth of the mixed powder to fill the die was adjusted in accordance with the monitored apparent density so that the weights of the mixed powders that fill the die were equal to each other in all batches. Under the condition B, changes in the apparent density of 0.01 Mg/m³ or less were regarded as measurement variations, and thus the filling depth was not adjusted. Table 2 shows the measurement results of the weights of the compacts produced under the two conditions.

Under the condition A, since the filling depth was not adjusted and was kept constant regardless of the change in the apparent density of the mixed powder, the weight of the compact was increased with increasing apparent density. In contrast, under the condition B, since the change in the apparent density of the mixed powder in the feeder was detected and the filling depth was adjusted in accordance with the change in the apparent density, the weight of the compact was substantially constant and the variation (standard deviation) in the weight of the compact was suppressed. In other words, when a powder compact is produced by adjusting the filling depth in the compaction operation in accordance with the apparent density measured by using the method for measuring an apparent density according to the present invention, the variation in the weight of produced powder compacts is decreased, which leads to a suppression of the variation in the quality of sintered compacts.

TABLE 2

| | | Condition A | | Condition B | | | |
|---|---|---|---|---|---|---|---|
| Compact No. | Apparent density of mixed powder *1 (Mg/m³) | Filling depth (mm) | Weight of compact (g) | Amplitude of alternating magnetic flux (V) | Apparent density *2 (Mg/m³) | Filling depth (mm) | Weight of compact (g) |
| 1 | 3.20 | 41.8 | 198.2 | 0.5173 | 3.30 | 41.8 | 198.3 |
| 2 | 3.20 | 41.8 | 198.3 | 0.5174 | 3.30 | 41.8 | 198.2 |
| 3 | 3.20 | 41.8 | 198.3 | 0.5175 | 3.30 | 41.8 | 198.3 |
| 4 | 3.20 | 41.8 | 198.3 | 0.5174 | 3.30 | 41.8 | 198.3 |
| 5 | 3.20 | 41.8 | 198.3 | 0.5176 | 3.31 | 41.8 | 198.3 |
| 6 | 3.20 | 41.8 | 198.3 | 0.5175 | 3.30 | 41.8 | 198.3 |
| 7 | 3.20 | 41.8 | 198.3 | 0.5173 | 3.30 | 41.8 | 198.3 |
| 8 | 3.20 | 41.8 | 198.3 | 0.5172 | 3.29 | 41.8 | 198.3 |
| 9 | 3.20 | 41.8 | 198.3 | 0.5173 | 3.30 | 41.8 | 198.3 |
| 10 | 3.20 | 41.8 | 198.3 | 0.5174 | 3.30 | 41.8 | 198.3 |
| 11 | 3.26 | 41.8 | 202.2 | 0.5191 | 3.36 | 41.1 | 198.5 |
| 12 | 3.26 | 41.8 | 202.1 | 0.5192 | 3.36 | 41.1 | 198.4 |
| 13 | 3.26 | 41.8 | 202.1 | 0.5191 | 3.36 | 41.1 | 198.3 |
| 14 | 3.26 | 41.8 | 202.1 | 0.5191 | 3.36 | 41.1 | 198.3 |
| 15 | 3.26 | 41.8 | 202.1 | 0.5192 | 3.36 | 41.1 | 198.3 |
| 16 | 3.26 | 41.8 | 202.1 | 0.5192 | 3.36 | 41.1 | 198.3 |

TABLE 2-continued

| Compact No. | Apparent density of mixed powder *1 (Mg/m³) | Condition A | | Condition B | | | |
| --- | --- | --- | --- | --- | --- | --- | --- |
| | | Filling depth (mm) | Weight of compact (g) | Amplitude of alternating magnetic flux (V) | Apparent density *2 (Mg/m³) | Filling depth (mm) | Weight of compact (g) |
| 17 | 3.26 | 41.8 | 202.2 | 0.5191 | 3.36 | 41.1 | 198.3 |
| 18 | 3.26 | 41.8 | 202.1 | 0.5190 | 3.35 | 41.1 | 198.4 |
| 19 | 3.26 | 41.8 | 202.1 | 0.5191 | 3.36 | 41.1 | 198.3 |
| 20 | 3.26 | 41.8 | 202.1 | 0.5191 | 3.36 | 41.1 | 198.3 |
| Average | — | — | 200.2 | — | | — | 198.3 |
| Standard deviation | — | — | 1.97 | — | | — | 0.06 |

*1 Apparent density measured in accordance with JIS Z 2504:2000
*2 Apparent density (Mg/m³) = Amplitude of alternating magnetic flux (V) × A + B
A = 34.946, B = −14.782

INDUSTRIAL APPLICABILITY

According to the present invention, the apparent density of a metal powder can be measured with a high precision by using simple equipment without directly contacting the metal powder in a vessel. Therefore, the apparent density of a powder held in a hopper or a feeder of the powder compact manufacturing line can be measured in an on-line manner without stopping the manufacturing line. Furthermore, in the process of producing a mixed powder by mixing a raw material powder and auxiliary raw materials with each other at a specified ratio using a mixer, a mixed powder having a desired apparent density can be produced by measuring, in an on-line manner, the apparent density of the powder during the mixing operation in the mixer, which produces industrially significant effects.

What is claimed is:

1. A method for measuring and adjusting an apparent density of a metal powder or a mixed powder, the method comprising:
   holding a metal powder or a mixed powder containing a metal powder in a vessel;
   applying an alternating magnetic flux to the metal powder or the mixed powder using an exciting coil disposed outside the vessel;
   detecting an alternating magnetic flux passed through the metal powder or the mixed powder using a search coil disposed outside the vessel; and
   determining an apparent density of the metal powder or the mixed powder from an amplitude of the detected alternating magnetic flux using a calibration curve representing a correlation between the apparent density of the metal powder or the mixed powder and the amplitude of the alternating magnetic flux prepared in advance,
   wherein the vessel is disposed outside turns of the exciting coil and turns of the search coil.

2. The method according to claim 1, wherein a frequency of the alternating magnetic flux applied to the metal powder or the mixed powder is 10 Hz or more and 10 kHz or less.

3. The method according to claim 1, wherein the metal powder or the mixed powder is the mixed powder.

4. The method according to claim 1, wherein the vessel is a hopper or a feeder, and the hopper or feeder is of a powder manufacturing line or of a powder compact manufacturing line.

5. The method according to claim 1, wherein the calibration curve is expressed as Equation 1:

$$\text{(Apparent density of metal powder or mixed powder)} = \text{(Amplitude of alternating magnetic flux)} \times A + B \quad (1),$$

where A and B are constraints determined from measurement results of the apparent density of the metal power or the mixed powder and the amplitude of the alternating magnetic flux by using a least-squares method.

6. The method according to claim 1, wherein the holding step includes holding the mixed powder in the vessel and the method further comprises adjusting a constitution of the mixed powder based on the determined apparent density.

7. The method according to claim 1, further comprising transporting the metal powder or the mixed powder on-line through a powder manufacturing line or a powder compact manufacturing line.

* * * * *